(12) United States Patent
Shikata (10) Patent No.: US 8,273,025 B2
(45) Date of Patent: Sep. 25, 2012

(54) ULTRASOUND PROBE

(75) Inventor: Hiroyuki Shikata, Tochigi-ken (JP)

(73) Assignees: Kabushiki Kaisha Toshiba, Tokyo (JP); Toshiba Medical Systems Corporation, Tochigi-Ken (JP)

( * ) Notice: Subject to any disclaimer, the term of this patent is extended or adjusted under 35 U.S.C. 154(b) by 159 days.

(21) Appl. No.: 12/779,186

(22) Filed: May 13, 2010

(65) Prior Publication Data

US 2011/0282211 A1 Nov. 17, 2011

(51) Int. Cl.
*A61B 8/00* (2006.01)
(52) U.S. Cl. ............. 600/437; 600/439; 600/459; 601/2
(58) Field of Classification Search ............ 600/437, 600/439, 459; 601/2
See application file for complete search history.

(56) References Cited

U.S. PATENT DOCUMENTS

| 5,560,362 A * | 10/1996 | Sliwa et al. .................. 600/439 |
| 2008/0146924 A1 * | 6/2008 | Smith et al. .................. 600/437 |

* cited by examiner

*Primary Examiner* — Tse Chen
*Assistant Examiner* — Baisakhi Roy
(74) *Attorney, Agent, or Firm* — Knoble Yoshida & Dunleavy, LLC (57) ABSTRACT

An ultrasound probe having a forced cooling system for circulating a liquid through a probe cable. The ultrasound probe comprised of a handle unit including a plurality of ultrasound transducers, a flexible cable connected to the handle unit and a connector unit coupled to the cable. The cable includes a plurality of electric signal lines and a cooling liquid circulation flow channel. The circulation flow channel is comprised of an outward path for transmitting the cooling liquid from the connector unit to the handle unit, and a return path for transmitting the cooling liquid from the handle unit to the connector unit. At least either one of the outward path or the return path is comprised of a plurality of thin tubes.

13 Claims, 10 Drawing Sheets

| NUMBER OF TUBES | 1 | 4 | 7 | 11 | 30 | 50 | 70 | 100 |
|---|---|---|---|---|---|---|---|---|
| INTERNAL DIAMETER OF A TUBE (mm) | 2 | 1 | 0.75 | 0.6 | 0.36 | 0.28 | 0.238 | 0.2 |
| WALL THICKNESS OF A TUBE (mm) | 1 | 0.4 | 0.3 | 0.2 | 0.08 | 0.05 | 0.05 | 0.05 |

FIG. 10

ULTRASOUND PROBE

CROSS-REFERENCE TO RELATED APPLICATIONS

This application incorporated incorporates Japanese Patent Application No. 2009-114374 filed on May 11, 2009 herein by reference in its entirety.

BACKGROUND OF THE INVENTION

A. Field of the Invention

The present invention relates to an ultrasound probe to be used with an ultrasound diagnosis apparatus, and more particularly to an ultrasound probe having a forced cooling system for circulating a liquid through a flexible cable connecting the ultrasound probe.

B. Background of the Invention

An ultrasound probe is detachably coupled to an ultrasound diagnosis apparatus for imaging an internal status of an object through ultrasounds. The ultrasound probe includes a handle unit including a tip portion for, making contact on a patient body surface, a cable connected to the handle unit, and a connector unit for connecting the cable to an ultrasound diagnosis apparatus. Usually, to freely operate the handle unit by an operator, a flexible cable having around two (2) meters in length for connecting the handle unit to the connector unit.

In an array type ultrasound probe, particularly in a two-dimensional (2D) array ultrasound probe, ultrasound transmissions and receptions are performed through several thousands of transducers. Recently, in a 2D array ultrasound probe, a part of the ultrasound transmission and reception functions by the ultrasound diagnosis apparatus is executed by an electronic circuit provided in the ultrasound probe. Thus, an electronic circuit in a handle unit of the 2D array ultrasound probe performs ultrasound transmission functions and a part of ultrasound reception functions.

To transmit and receive various signals such as ultrasound data signals, control signals and power supplying signals, between the electronic circuit in the handle unit and the ultrasound diagnosis apparatus main body, a plurality of electric signal lines passes through in the flexible cable. The electric signal lines include power supplying twisted pair wires, control signal lines and very thin coaxial lines for transmitting and receiving ultrasound signals. Typically, more than two hundred of the electric signal lines are included in the flexible cable. Usually, each of the signal lines has an external diameter $\phi$ of about 0.3 millimeter. The electric signal lines are twisted together and adjusted so that a cross-sectional plane of a whole cable is configured to a circular shape. The whole cable is covered by a shield member and an outer envelope member.

The electronic circuit in the probe is mounted on a substrate provided in a handle unit as an integrated circuit (IC). During the time of the ultrasound transmissions and receptions, the IC in the handle unit generates heat of several watts (1~2 W) by consuming electric power. While the heat generated in the handle unit is radiated through the probe housing, a part of the heat is transmitted to a tip portion of the probe. A plurality of ultrasound transducers is mounted in the tip portion of the probe. Consequently, in the ultrasound transmission time, the plurality of transducers also generates the heat. As a result, the heat component transferred from the IC and the other heat component generated in each of the transducers are summed up and increase the temperature of the tip portion of the probe that contacts a patient.

The temperature increase of the tip portion of the probe causes a low temperature burn on the patient. To prevent this, an upper limit of the temperature increase of the tip portion of an ultrasound probe has been determined by the international standard (IEC 60601). While the heat generated from the transducers is proportional to the acoustic energy emitted into a living body, the heat generated from the IC contains a component proportional to the transmission energy and a constant component due to the bias current for the transmission and reception circuit.

Usually, to keep the temperature increase of the tip portion contacting a patient under a limited temperature, the total power consumption of the transducers is controlled by limiting the transmission voltage. In the 2D-array probe having an IC in the handle unit, since the IC generates the heat, it needs to keep a transmission voltage that is lower than that in the normal probe in which an electronic circuit is not provided in order to keep the temperature of the patient contacting portion of the probe under the limited temperature. At the lower transmission voltage, a sound pressure of the transmission ultrasound emitted into the living body is also reduced, and the receiving voltages of echo signals are reflected from the living body become small. As a result, the signal to noise (S/N) ratio is reduced. Further, since a generation ratio of harmonic contents proportional to a square of the transmitting sound pressure also becomes a small, it becomes difficult to improve an image quality by receiving the harmonic contents.

Figure 5:
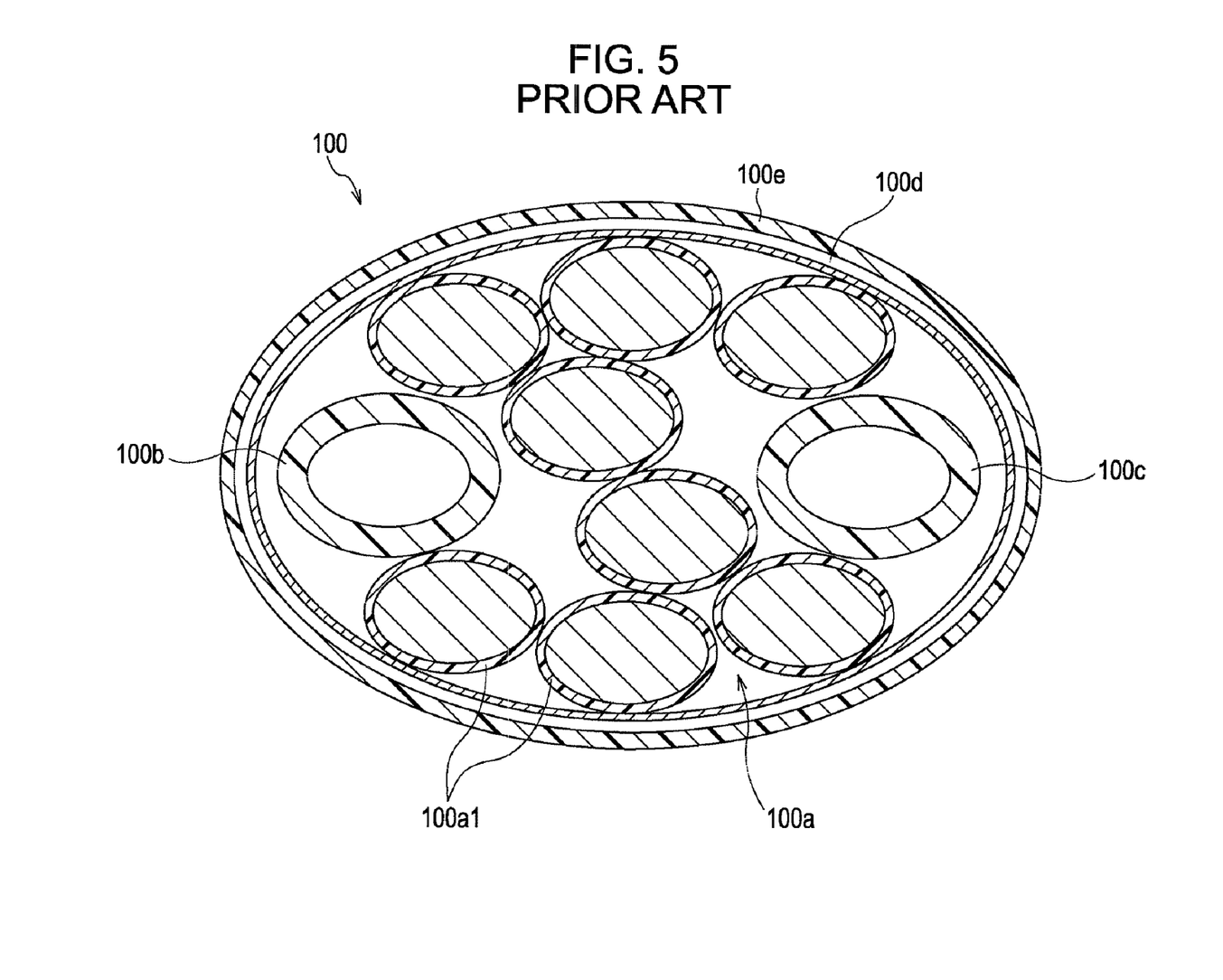
FIG. 5 illustrates a crashed status in a cable of the prior art.

To avoid these problems, an ultrasound probe having a forced cooling system has been proposed for cooling the IC provided in a handle unit by circulating a cooling liquid around the IC (for instance, see Japanese Patent Application Publication 2003-38485). The forced cooling system includes a pump provided in an ultrasound diagnosis main body or a connector unit of an ultrasound probe and two hollow tubes provided in the cable for circulating a cooling liquid in the handle unit through the cable. Thus, as shown in FIG. 5, one of the two hollow tubes is used as a cooling outward path for flowing the cooling liquid from the connector unit to the handle unit and the other is used as a cooling return path for returning the cooling liquid from the handle unit to the connector unit.

Once the cooling liquid has returned to the connector unit after absorbing the heat in the handle unit, it needs to radiate the absorbed heat before re-circulating through the cooling outward path in order to keep the cooling efficiency. Usually, the heat radiation from the connector unit is performed by a heat sink and/or heat radiating fins in the connector unit. Further, an air cooling fan and a heat outfall are provided in the connector unit, if necessary. It is also possible to perform the heat radiation by a heat connecting member on the connector unit connected to the ultrasound diagnosis apparatus so as to directly transfer the heat to the ultrasound diagnosis apparatus having a big heat capacity.

Usually, a rubber tube or a plastic tube made of an urethane resin or a fluorine resin is used as the circulating cooling liquid flow channel. An internal diameter $\phi$ of the flow channel is around 1.5 to 2.0 millimeters in accordance with a required liquid flow amount and a pumping power of the pump provided in the connector unit. To perform various diagnoses by operating the handle unit at various angles and positions, the cable should be flexible. Thus, the cable is bent and deformed in accordance with the operation of the handle unit. If the tube strength is insufficient, the tube is bent by the deformation of the flexible cable. As a result, the temperature of the patient contacting portion increases due to the insufficient amount of the cooling liquid supply. This is a serious problem.

To avoid this problem, it needs to keep the wall thickness of the cooling tube more than about one (1) millimeter. As a result, usually, an external diameter φ of the cooling tube becomes about 3.5 to 4.0 millimeters. Thus, the cable is needed to include two tubes for a cooling liquid outward path and a liquid return path in it, and each tube has an external diameter φ of about 4.0 millimeters.

However, when the flexible cable is manufactured by including a plurality of electric signal lines together with the two cooling tube in it, the difference in hardness and diameter between the electric signal line and the cooling tube generates another problem. Typically, the cooling tube having a relatively thick external diameter φ of four (4) millimeters is harder than the electric signal lines, each having a smaller diameter. As a result, it becomes difficult to easily twist the thin electric signal lines together with the cooling tube. Further, the hardness of the cooling tubes affects the flexibility of the ultrasound probe. Thus, a free operability of the probe is badly influenced.

Further, when the cable is sharply bent during the operation, it happens to pinch or bend the tube filled with the circulating liquid in an inner flow cavity. In such a case, since the amount of the cooling liquid is extremely reduced, the temperature of the tip portion of the probe is largely increased. As explained before, the temperature increase of the tip portion causes a low temperature burn of the patient. As the wall thickness of the cooling tube is increased to avoid the buckling, the flexibility of the cable is decreased. Further, since the external diameter of the cable is also increased, the operability of the probe is extremely reduced.

SUMMARY OF THE INVENTION

The present invention addresses the above-mentioned and other problems and drawbacks, and provides a novel ultrasound probe having an IC in a probe head that can increase the free operability of the probe and cooling efficiency for avoiding heat generation from the probe.

The ultrasound probe according to one embodiment of the present invention includes:

a handle unit including a plurality of transducers to transmit and receive ultrasound;

a flexible cable connected to the handle unit;

a connector unit connected to the flexible cable for coupling the flexible cable to an ultrasound diagnosis apparatus; and a cooling liquid circulating system configured to circulate a liquid between the handle unit and the connector unit;

wherein the cable includes a plurality of electric signal lines and a circulation flow channel for the cooling liquid circulating system;

wherein the liquid circulation flow channel is comprised of;

a cooling liquid outward path configured to flow the cooling liquid from the connector unit to the handle unit, and a cooling liquid return path configured to flow the liquid from the handle unit to the connector unit, wherein at least either one of the cooling liquid outward path and the liquid return path is comprised of a plurality of thin follow tubes.

BRIEF DESCRIPTION OF THE DRAWINGS

The accompanying drawings, which are incorporated in and constitute part of this specification, illustrate various embodiments and/or features of embodiments of the present invention, and together with the description, serve to explain embodiments of the present invention. Where possible, the same reference number will be used throughout the drawings to describe the same or like parts. In the drawings.

DESCRIPTION OF THE EMBODIMENTS

Figure 1:
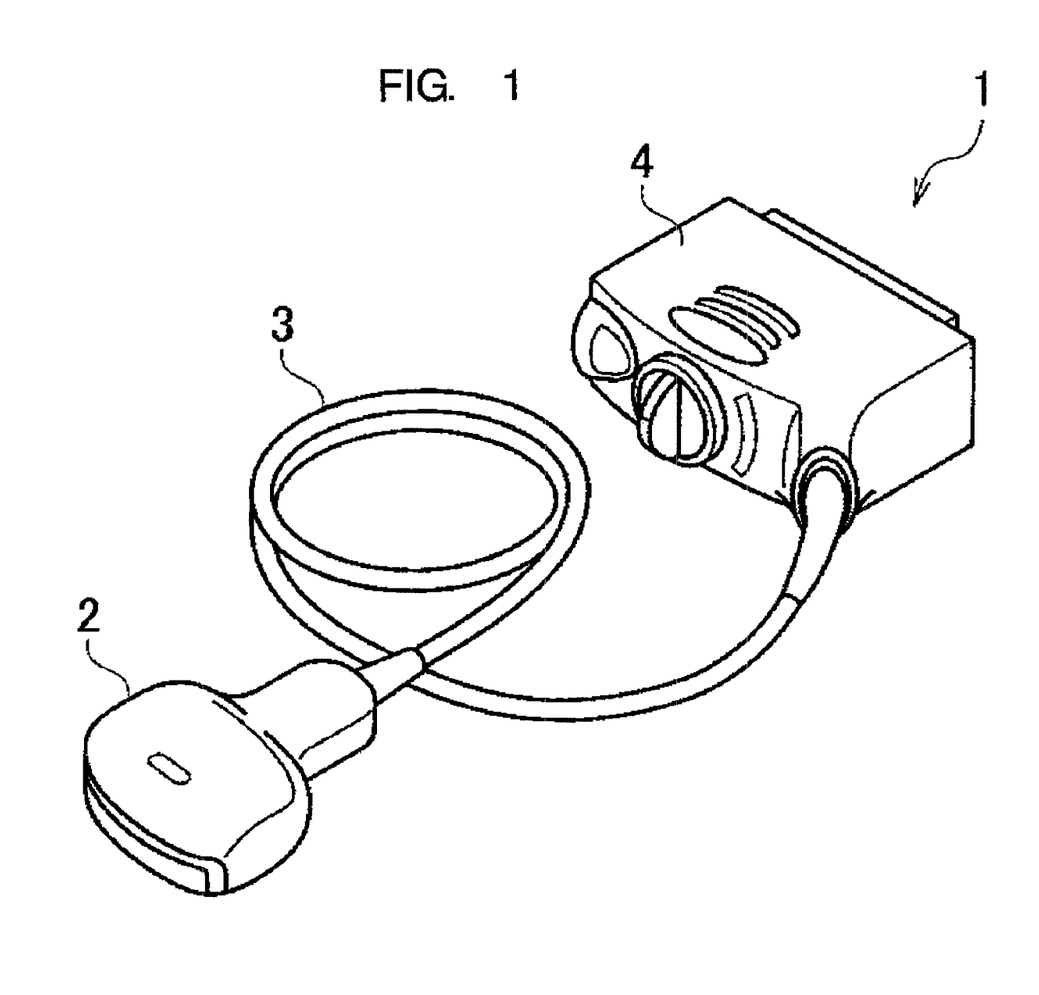
FIG. 1 is a perspective view of an ultrasound probe consistent with one embodiment of the present invention.

FIG. 1 illustrates an ultrasound probe 1 consistent with the present invention. The ultrasound probe 1 includes a handle unit 2, a flexible cable 3 connected to the handle unit 2 and a connector unit 4 coupled to the cable 3.

Figure 2:
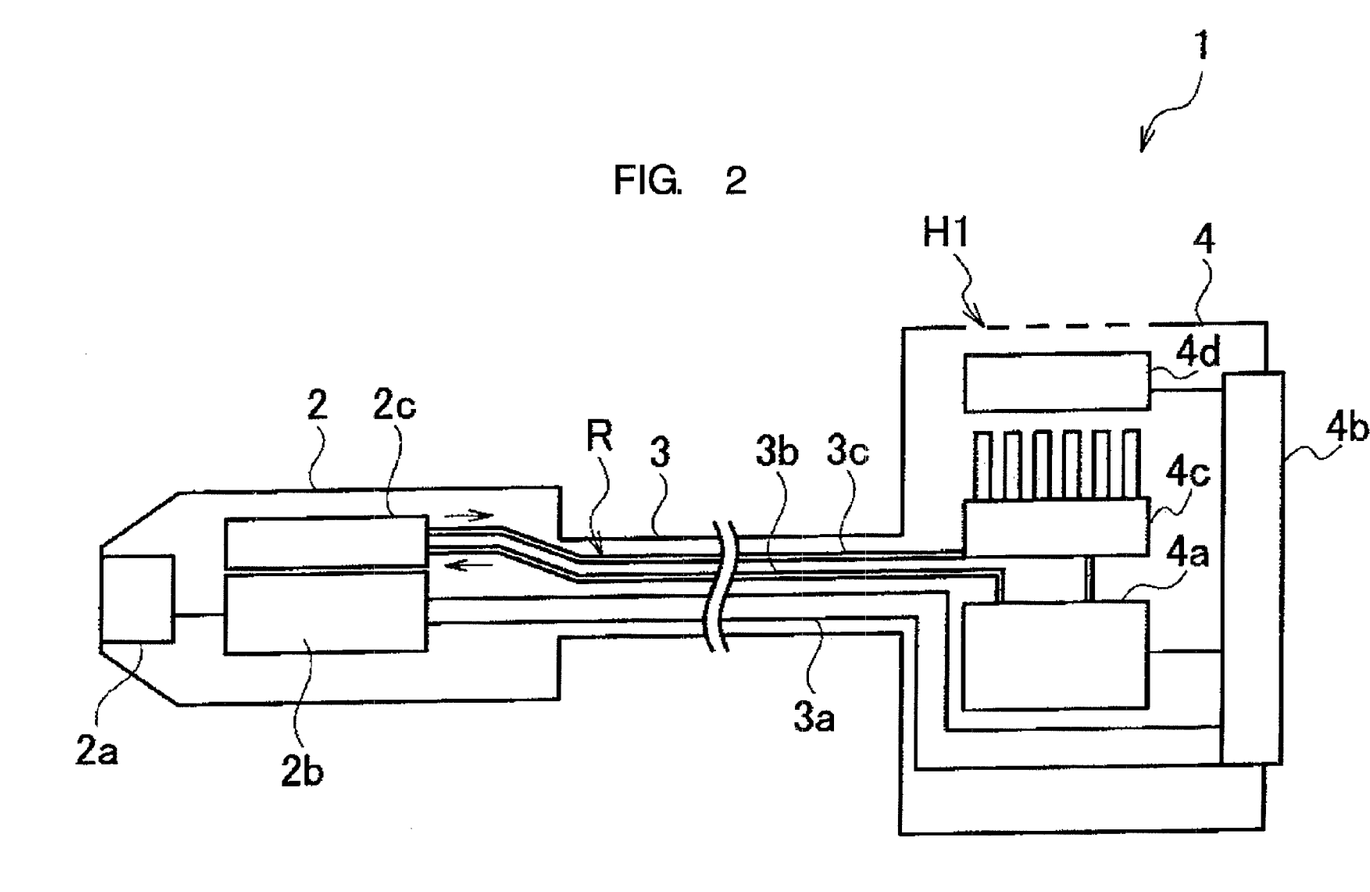
FIG. 2 is a cross-sectional view of the ultrasound probe as shown in FIG. 1.

As illustrated in a cross-sectional view in FIG. 2, the handle unit 2 includes one of a plurality of ultrasound transducers 2a for transmitting and receiving ultrasound, an electronic circuit 2b for performing the ultrasound transmissions/reception functions and a heat sink 2c for cooling the electronic circuit 2b. Each of the plurality of ultrasound transducers 2a provided in the tip portion of the handle unit 2 transmits ultrasound onto an object and receives reflected waves from the object. The handle unit 2 is operated to make contact on a patient body by an operator.

The cable 3 includes a collective entity 3a of a multiplicity of electric signal lines and a circulation flow channel R for circulating the cooling liquid. The circulation flow channel R is constructed by a first tube collective entity 3b as an outward path for transmitting the cooling liquid from a pump provided in the connector unit 4, and a second tube collective entity 3c as a return path of the cooling liquid from the heat sink 2c in the handle unit. The signal lines collective entity 3a is connected to the electronic circuit 2b provided in the handle unit 2. The first tube collective entity 3b and the second tube collective entity 3c of the circulation flow channel R are communicated with each other through the heat sink 2c in the handle unit 2 for constructing the cooling liquid circulating flow channel for the handle unit 2.

The connector unit 4 includes a pump 4a for circulating the cooling liquid in the circulation flow channel R, a connector 4b for electrically coupling to the ultrasound diagnosis apparatus, a second heat sink 4c a second heat sink 4c having radiation fins and an exhaust fan 4d. The pump 4a and the exhaust fan 4d are electrically connected to the connector 4b and are driven by a power supplied from the ultrasound diagnosis apparatus. The signal lines collective entity 3a is also electrically connected to the connector 4b. The electronic circuit 2b in the handle unit 2 performs signal transmissions and receptions for the ultrasound diagnosis apparatus through the signal lines collective entity 3a. The heat sink 4c in the connector unit 4 is provided on a midway of the second tube collective entity 3c to partially form the return path of the circulation flow channel R. The exhaust fan 4d is provided adjacently to the heat sink 4c in the connector unit 4 for discharging the heat from the connector unit 4 through an exhaust opening H1 (FIG. 2).

Each of the ultrasound transducers 2a in the handle unit 2 is connected to the electronic circuit 2b. The electronic circuit 2b generates transmission signals for transmitting ultrasound from the ultrasound transducers 2a that receive ultrasound reflected from the object. The ultrasound transducers 2a convert and transmit the received signals to the ultrasound diagnosis apparatus.

Figure 3:
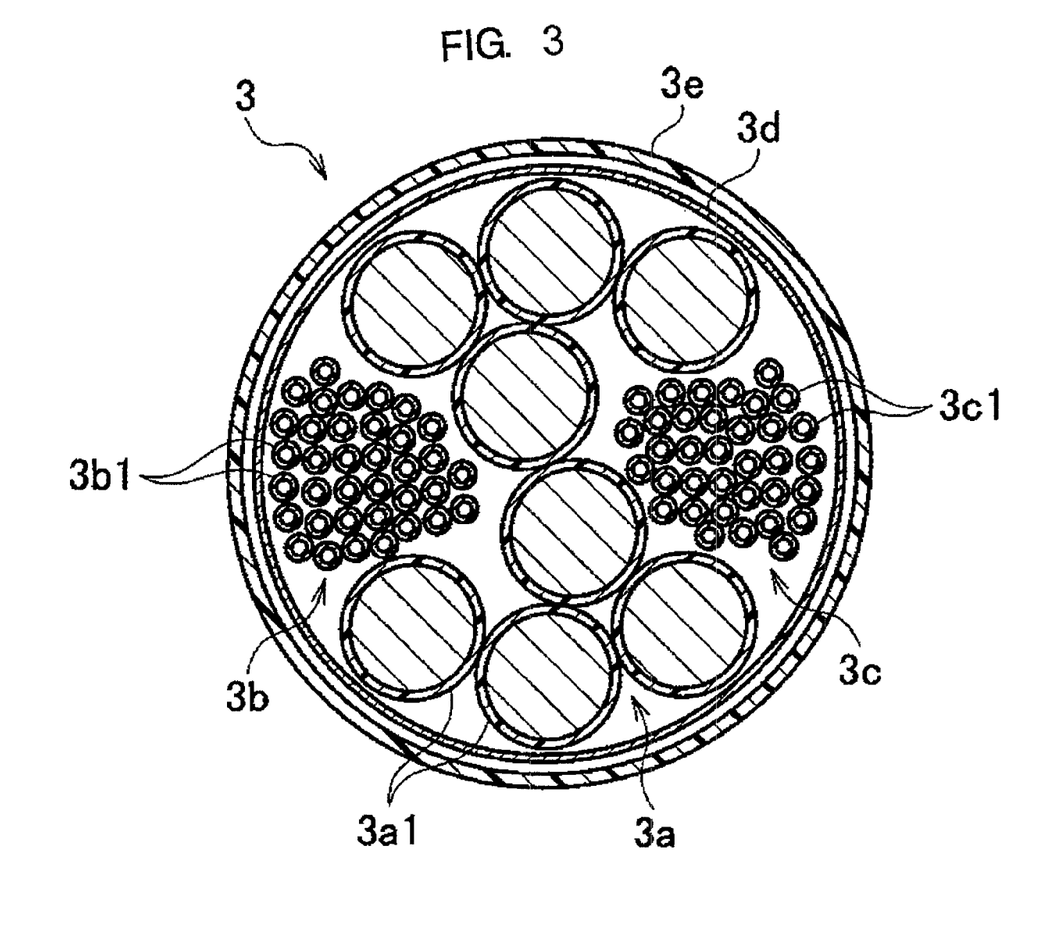
FIG. 3 is a cross-sectional view of the cable portion of the ultrasound probe as shown in FIGS. 1 and 2.

FIG. 3 is a cross-sectional view of the cable 3. In the cable 3, the signal lines collective entity 3a, the outward path tube collective entity 3b and the return path tube collective entity 3c, while the collective entities 3b and 3c construct the circulation flow channel R, all of the above described collective entities 3a, 3b and 3c are covered by a single shield body 3d and a single external covering body 3e.

The signal lines collective entity 3a is constructed by twisting together a multiplicity of signal lines 3a1, such as twisted pair lines or thin coaxial lines. It is also possible to twist together another kind of lines, if necessary.

The outward path tube collective entity 3b of the circulation flow channel R is constructed by bundling a plurality of thin tubes 3b1 in parallel, each diameter is much thinner than the diameter of each of the electric signal lines 3a1 so as to flow the cooling liquid from the connector unit 4 to the handle unit 2. The plurality of the thin tubes 3b1 is bundled as one collective entity through the pressure bonding or the thermal adhesion to connect to the heat sink 2c in the handle unit 2. Similarly, in the connector unit 4, the plurality of thin tubes 3b1 is bundled as one collective entity in order to connect to the pump 4a.

The return path tube collective entity 3c of the circulation flow channel R is also constructed by bundling a plurality of thin tubes 3c1 in parallel, each diameter is much thinner than the diameter of each of the electric signal lines 3a1 so as to flow the cooling liquid from the handle unit 2 back to the connector unit 4. As shown in FIG. 2, the return path tube collective entity 3c is also collecting the cooling liquid into a single tube collective entity in the handle unit 2 and is connected to the heat sink 2c in the handle unit 2. The return path tube 3c is further collecting the cooling liquid as a single tube collective entity in the connector unit 4 and is coupled to the pump 4a through the heat sink 4c in the connector unit 4.

The thin tubes 3b1 and 3c1 forming the circulation flow channel R are made by plastic tubes, for instance, of a polyimide resin, a fluorine resin, or a polyether ether ketene (PEEK) resin.

The outward path tube collective entity 3b and the return path tube collective entity 3c are provided apart from each other in the cable 3. For instance, the outward path tube collective entity 3b and the return path tube collective entity 3c are provided adjacent to an inner surface of the external covering body 3e so as to face each other. Thus, as illustrated in FIG. 3, the outward path tube collective entity 3b is provided at an opposite position of the return path tube collective entity 3c in the cable 3.

Since the return path flows the liquid that has absorbed the heat generated from the IC 2b in the handle unit 2, the temperature of the return path is higher than one of the outward path that flows the cooled liquid through the radiation in the cable 3 and the connector unit 4. Thus, a temperature differences exists between the liquid flowing in the return path tube and in the outward path tube. Accordingly, the outward path tube collective entity 3b and the return path tube collective entity 3c are provided apart from each other to avoid deterioration in cooling efficiency due to heat exchange between them.

Figure 4:
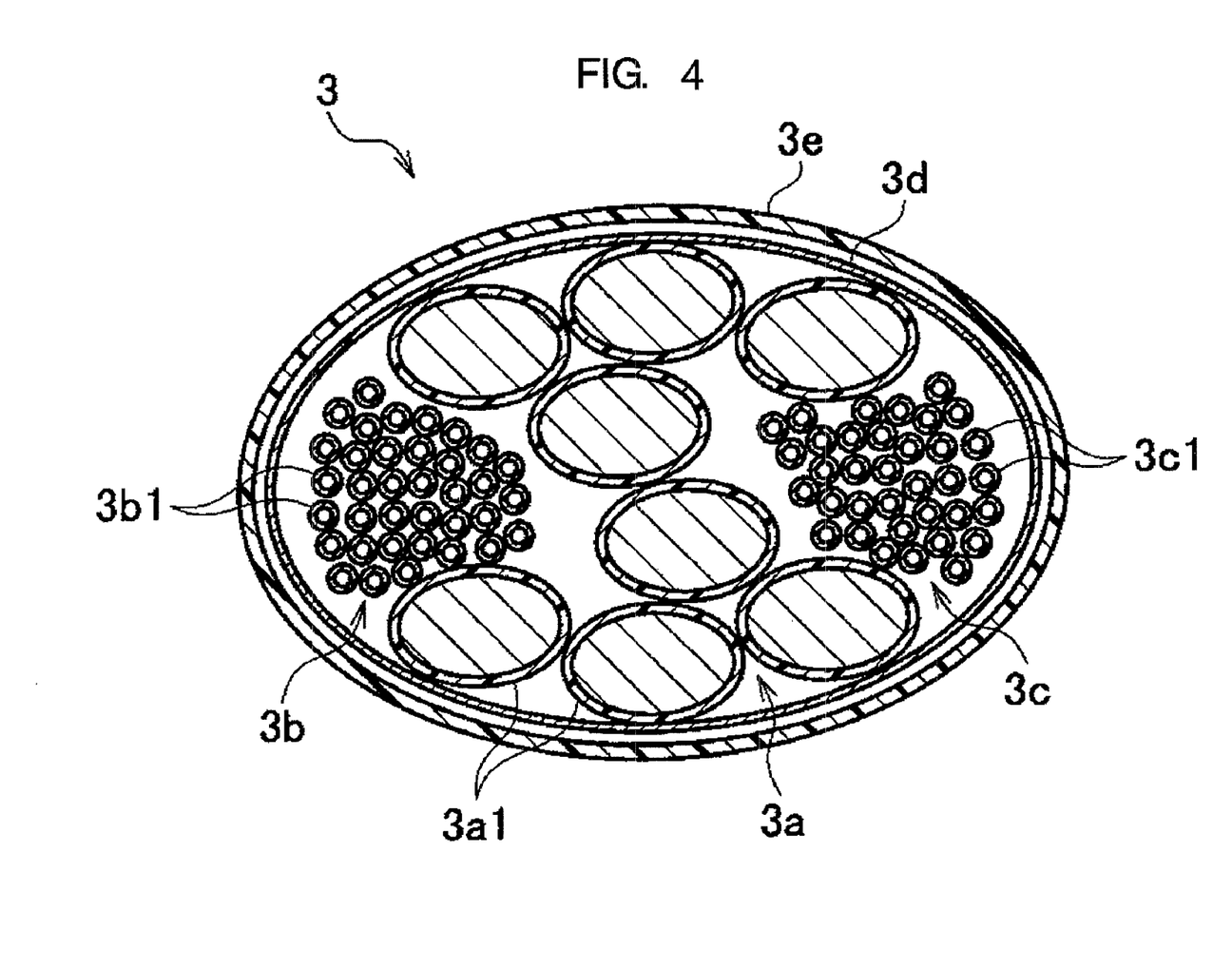
FIG. 4 illustrates a crashed status of the cable portion as shown in FIG. 3.

When the cable 3 is bent during the usage of the ultrasound probe 1 by an operator as illustrated in FIG. 4, the inside of the cable 3 is distorted and crushed. In such a state, while each of the collective electric signal lines 3a1, the shield body 3d and the external covering body 3e is crushed, each of the tubes 3b1 in the outward path tube collective entity 3b and the tubes 3c1 in the return path tube collective entity 3c is not crushed in the shield body 3d the cable 3 since each tube has room to move with respect to each other in the collective entity.

FIG. 5 illustrates a crushed state of the prior art cable 100 in which the circulation flow channel is comprised by a single tube outward path and a single tube return path. Thus, in the cable 100, a collective entity 100a1 of a plurality of electric signal lines, a single tube of the outward path 100b and a single tube for the return path 100c are covered by an a single shield body 100d and a single external covering body 100e. When the cable 100 is bent and crushed, all tubes in the shield body 100d and the external covering body 100e are also crushed. That is, in addition to each of the electric signal lines 100a1, both the outward path tube 100b and the return path tube 100c also are crushed. Thus, the amount of the cooling liquid is extremely reduced due to the deformity of the liquid circulation flow channel. Consequently, the cooling efficiency is also extremely reduced.

On the contrary, according to the cable construction shown in FIG. 3, even when the whole cable 3 is distorted by bending, the bending stress can be absorbed by shifting each of the tubes 3b1 and 3c1 within available room near the respective tube collective entities 3b and 3c. Consequently, distortion of each of the tubes 3b1 and 3c1 would be substantially eliminated. Further, when the cable is bent, since the curvature radius of the cable is relatively larger than the tube radius, the buckling of the tubes 3b1 and 3c1 is least likely to happen. Even when a buckling occurred in any tube, it is possible to keep a substantially original volume of the flow path by the remaining plurality of tubes 3b1 and 3c1. As a result, an extreme reduction in flow amount can be avoided.

Further, according to the cable construction shown in FIG. 3, it is possible to reduce an internal diameter of each of the tubes 3b1 and 3c1 while the circulation flow channel is kept by a necessary inner cavity section area. Since the tubes 3b1 and 3c1 of such a small internal diameter cannot be easily crushed, it becomes possible to reduce the wall thickness of the tubes. Consequently, heat-transfer efficiency from the tubes 3b1 and 3c1 into the exterior can be increased. Further, since large heat conductivity and a large surface area of the tubes can be obtained due to the thin wall thickness and the multiplicity, the heat-transfer efficiency between a refrigerant and a heating element can be also increased.

Further, according to the cable construction shown in FIG. 3, it becomes possible to twist together the circulation flow channel with the electric signal lines 3a1 in the cable 3, since the differences of the external diameters or the hardness between them become small. By reducing the whole external diameter of the cable 3, a flexible cable of a small radius can be made in order to increase operability of the cable. Further, even if a flow amount is increased, pressure damages are decreased, since it becomes difficult to generate a turbulent flow due to the thin tube of the respective channels As explained above, according to the embodiment consistent with the present invention, at least either one of the outward path and the return path of the circulation flow channel R is constructed by a plurality of tubes that are thinner than the collective diameter of the signal lines. Consequently, it becomes possible to absorb the bending stress for the cable 3 by shifting each position of the respective tubes. Further, distortion of the tubes is least likely to happen. Even if a buckling occurred in some of tubes, it is possible to keep the flow amount by keeping a substantially original volume of the flow path through the remaining plurality of tubes.

According to the embodiment consistent with the present invention, it becomes possible to reduce each internal diameter of the respective tubes with keeping a necessary inner cavity section area of the circulation flow channel. Since such a tube having a small internal diameter does not easily crush, a wall thickness of the tube can be made relatively thin so as to increase the heat-transfer efficiency to an outer side of the tubes. Further, it becomes possible to make the cable 3 thin so as to increase the flexibility. Thus, according to the ultrasound probe consistent with the present, the operability and the cooling ability can be increased.

In the embodiment consistent with the present invention, each of the plurality of tubes $3b1$ and $3c1$ are collected into a single tube in the connector unit 4 and connected to the pump 4a. This feature is a benefit to simplify the connection construction in comparison to connect each of the plurality of tubes to the pump. The connecting operation itself can be easily achieved. Further, each of the plurality of tubes $3b1$ and $3c1$ is made by a polyimide resin that has a low vapor permeability. As a result, since the cable is resistant to evaporation, an ultrasound probe of high reliability can be achieved.

Figure 6:
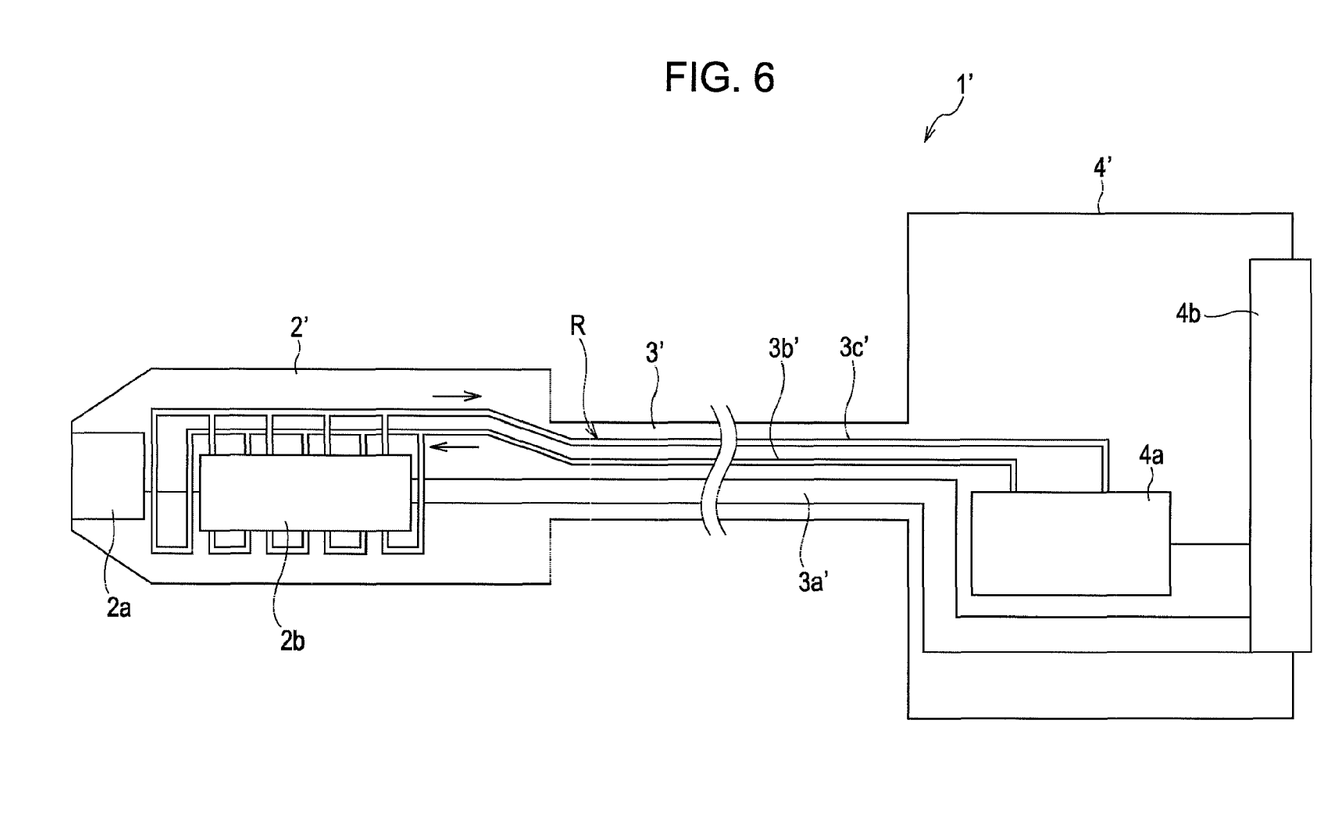
FIG. 6 is a cross-sectional view of the ultrasound probe consistent with another embodiment of the present invention.
Figure 7:
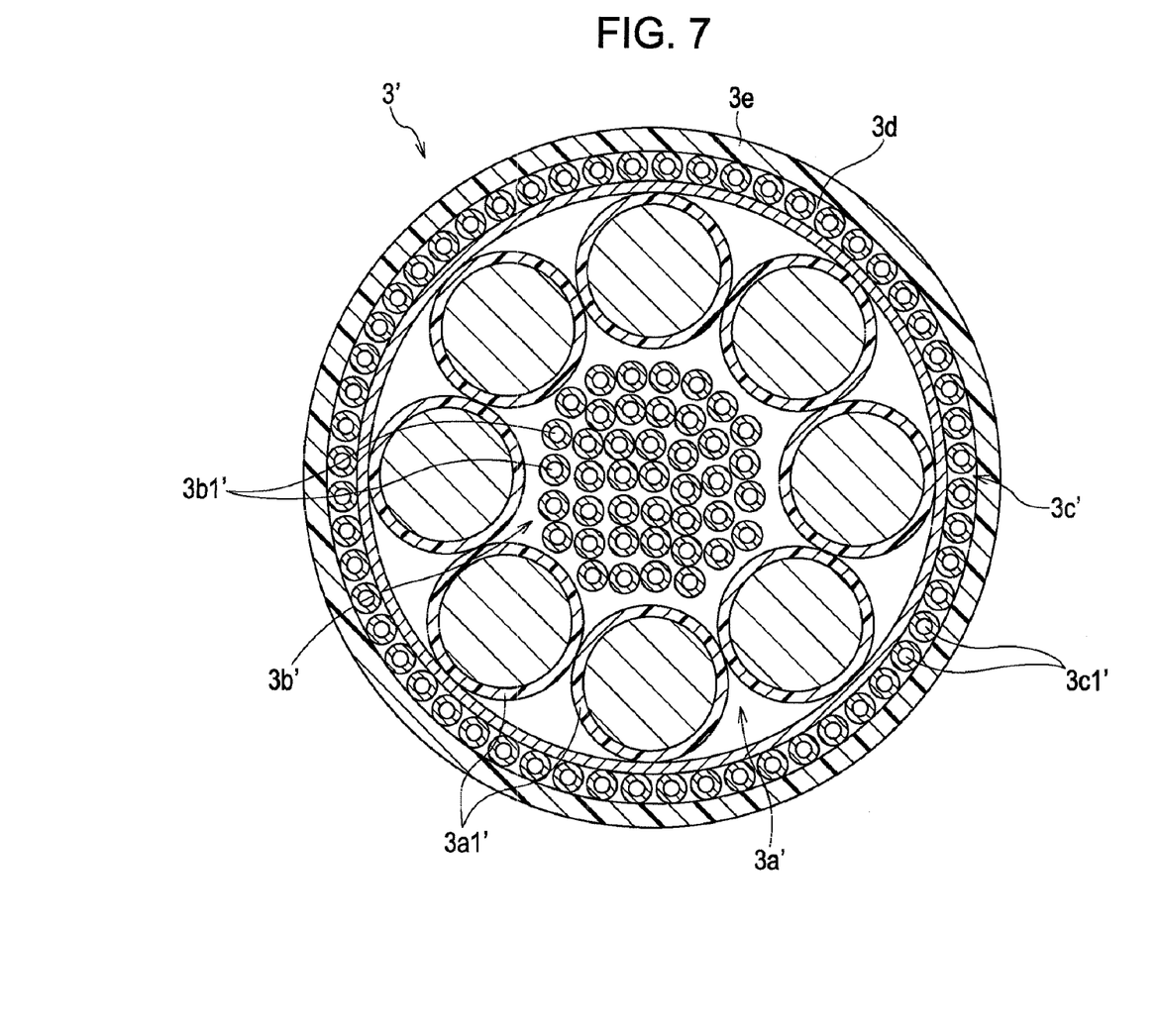
FIG. 7 is a cross-sectional view of the cable portion of the ultrasound probe as shown in FIG. 6.
Figure 8:
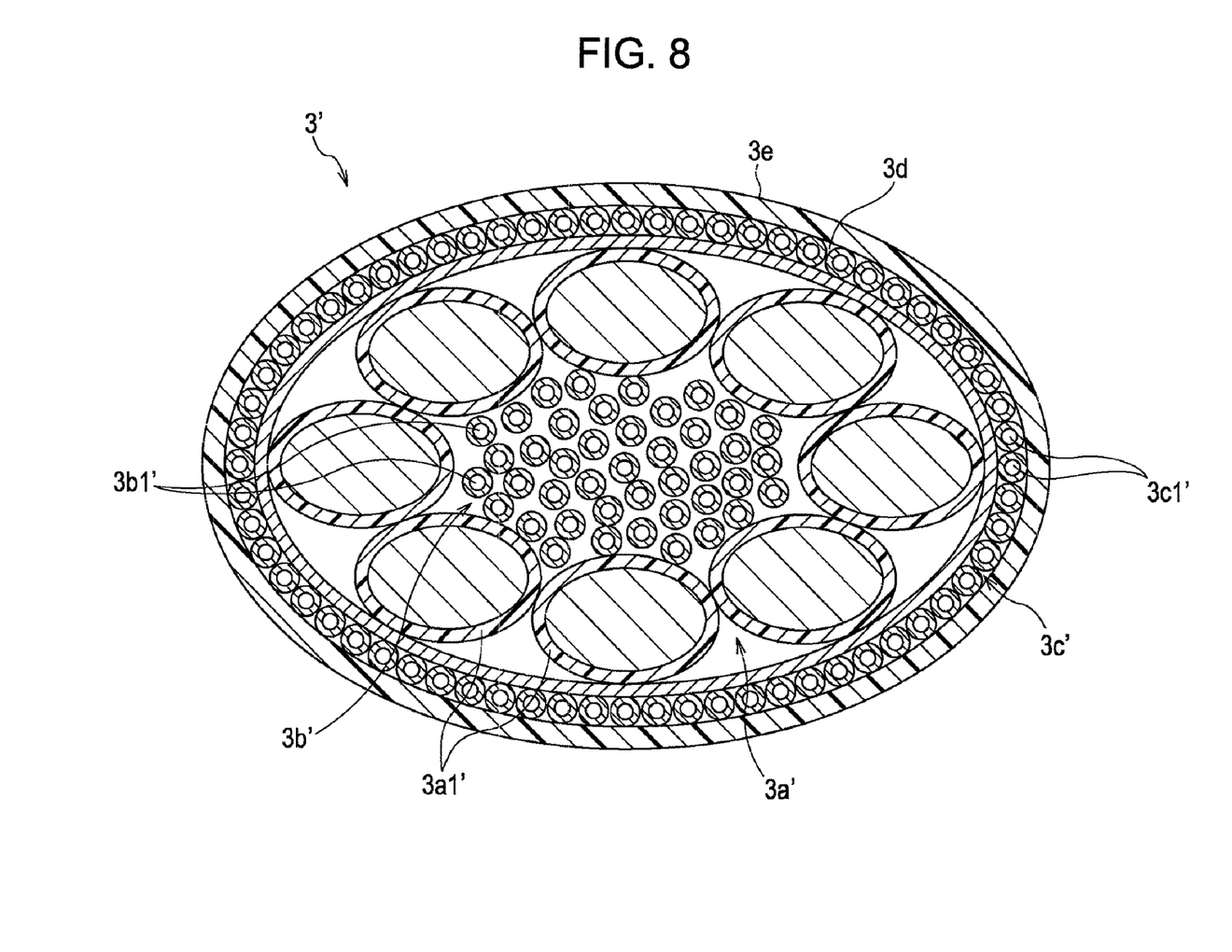
FIG. 8 illustrates a crashed status of the cable portion as shown in FIG. 7.

Referring to FIGS. 6 to 8, another embodiment of ultrasound probe 1' consistent with the present invention would be explained. To avoid a redundant explanation, the same units in the ultrasound probe 1 shown in FIG. 1 are omitted by attaching the same unit numbers.

In the ultrasound probe 1' shown in FIG. 6, to achieve heat-transfer of the electronic circuit $2b$, an outward path tube collective entity $3b$ and a return path tube collective entity $3c$ are provided so as to connect to the electronic circuit $2b$ at multiple locations. Further, the connector unit 4' lacks the heat sink $4c$, the exhaust fan $4d$ and the exhaust opening H1 that are provided in the embodiment shown in FIG. 2.

FIG. 7 illustrates a cross-section of the cable 3' shown in FIG. 6. As shown in figure, a plurality of thin return path tube $3b1'$ constructing a coolant outward path tube collective entity $3b'$ is provided at a center portion in an inside of a plurality of electric signal lines $3a1'$ that are provided in a circular shape in the cable 3'. Then, a plurality of thin return path tube $3c1'$ constructing a coolant return path tube collective entity $3c'$ is sparsely provided in a circular shape just between a cable external covering body $3e$ and the shield body $3d$ so as to have a moving tolerance with each other.

FIG. 8 illustrates a bent state of the cable 3 as shown in FIG. 7 during operation of the ultrasound probe 1 by an operator. When the cable 3 is bent, the cable external covering body $3e$, the shield body $3d$, each of the plurality of electric signal lines $3a1'$ and the plurality of coolant outward path tubes $3b1'$ provided at the center portion of the cable are placed in a crushed state. On the contrary, the plurality of coolant return path tube $3c1'$ sparsely provided between the cable external covering body $3e$ and on the shield body $3d$ can move so as to fill up the tolerance space provided between each other. Accordingly, the return path tubes $3c1'$ are not crushed.

By providing the coolant outward path of the plurality of tubes $3b1'$ at a center portion in the cable 3' and by providing the coolant return path of the plurality of tubes $3c1'$ just below the external covering body $3e$ distributed in a circle so as to keep a certain distance between the coolant outward path and the coolant return path, it can reduce the temperature of the circulating liquid. Further, since the plurality of tubes $3c1'$ is provided just below the external covering body $3e$, the increased temperature of the cooling liquid in the return path can be radiated into the air until reaching to the connector unit 4'.

By using the cable 3' of 2 meters in length, according to the embodiment, it is verified that the temperature of the circulating liquid sufficiently falls due to heat diffusion from the external covering body $3e$ of the cable 3'. Thus, since it does not need not to provide the inner heat sink $4c$ in the connector unit 4, the exhaust fan $4d$ and the exhaust opening H1, a miniaturization, a weight saving and a cost reduction can be achieved for the ultrasound probe 1'.

By taking out the exhaust opening H1 from the connector unit 4, it is possible to avoid a problem such as a reduced cooling ability due to clogging of an air filter and undesirable effects by the exhaust opening during cleaning and sterilization of the probe.

By providing the return path of a plurality of tubes $3c1'$ just below the external covering body $3e$ of the cable, it becomes unnecessary to provide a connector having a special structure for heat coupling to the ultrasound diagnosis apparatus. Thus, an additional cost of the ultrasound probe can be avoided.

According to this embodiment, it becomes possible to obtain a sufficient heat-transfer efficiency by putting the thin tubes $3b1'$ and $3c1'$ around in the handle unit 2. As a result, since the heat sink $2c$ becomes unnecessary, a weight saving and a miniaturization of the handle unit 2 are realized. Further, it becomes possible to increase the heat-transfer efficiency by uniformly providing the thin tubes $3b1$ and $3c1$ in the handle unit 2 or by providing the thin tubes $3b1$ and $3c1$ at a high density near the heat source.

Figure 9:
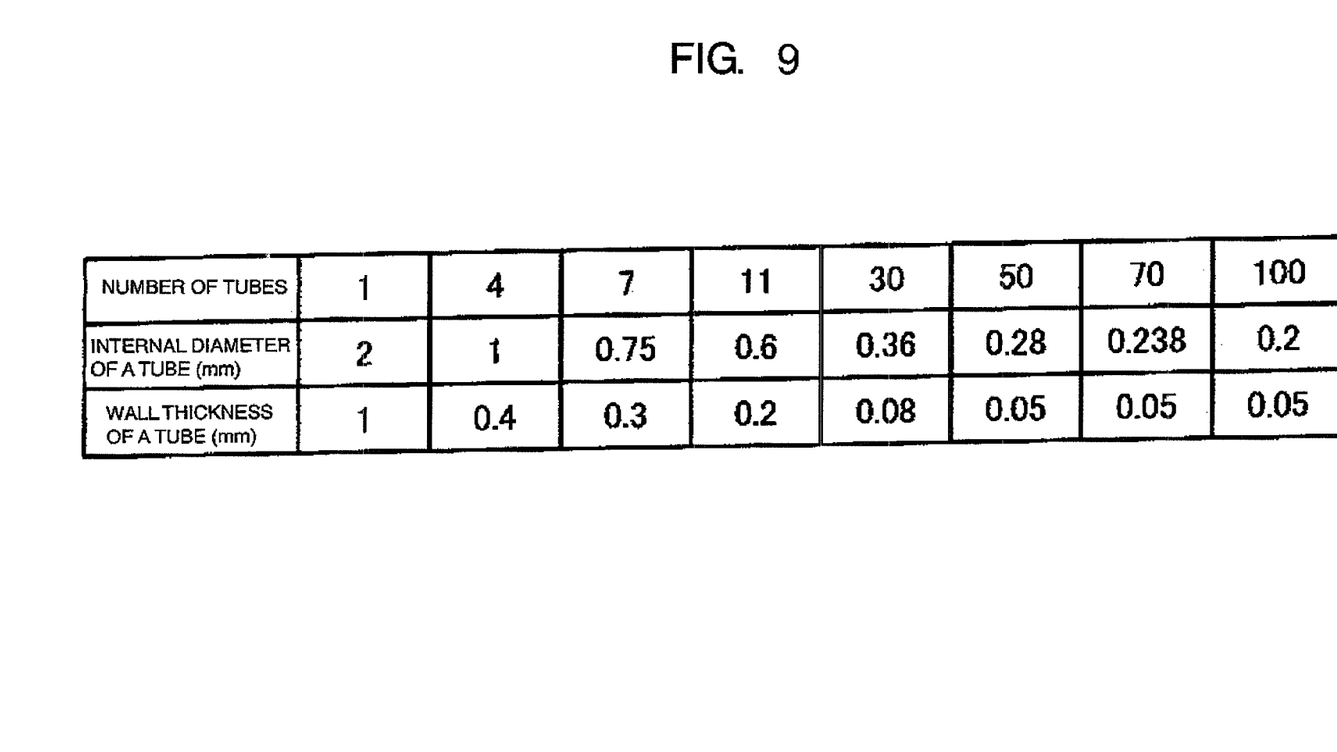
FIG. 9 is specification values illustrating relationships among a number of the cooling tubes, an internal diameter of the tubes and a wall thickness of the cooling tubes.

FIG. 9 is a specification value list illustrating relationships among the number of the cooling tubes, the internal diameter and the wall thickness of the respective tubes in this embodiment. Thus, the tube specification values are obtained by changing the number of the thin tubes $3b1'$ and $3c1'$ and substantially maintaining a total internal cavity sectional area of the tubes $3b1'$ and $3c1'$.

Figure 10:
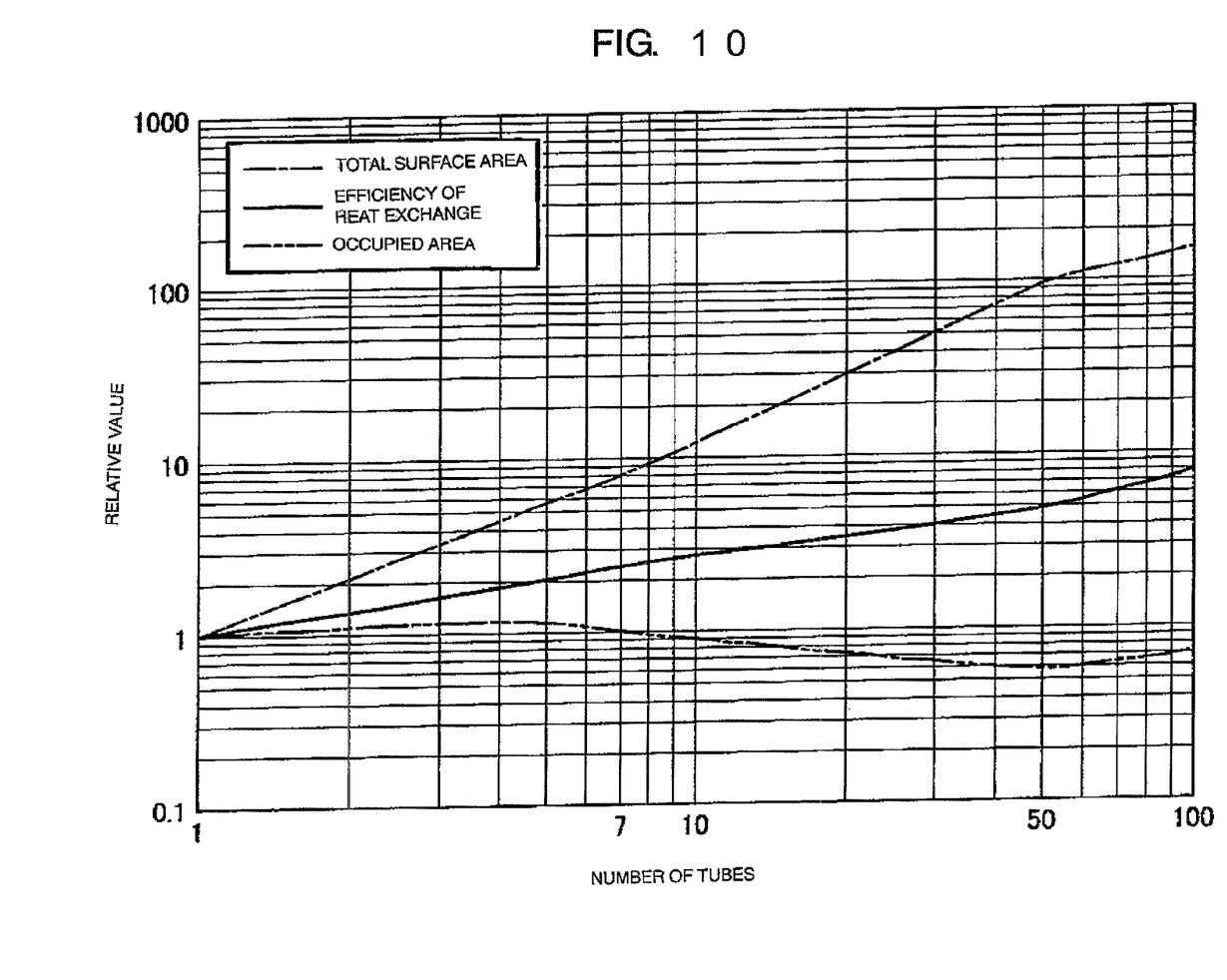
FIG. 10 is a graph illustrating relationships among the number of the cooling tubes, a total surface area, heat-transfer efficiency and an occupied area.

FIG. 10 is a graph illustrating heat-transfer efficiency on the tube surface that is calculated based on the total surface area, the occupied area and the wall thickness at relative values to the numbers as shown in FIG. 9 with reference to the surface made of a single tube. As illustrated in FIG. 10, when the number of the cooling liquid tubes is less than 7, the efficiency of heat exchange is decreased and the occupied area is increased. The larger a number of the cooling tubes $3b1'$ and $3c1'$ is provided, the larger a total surface area is obtained. Thus, as the internal diameter becomes smaller since they do not collapse easily, it becomes possible to make each of the tubes $3b1$ and $3c1$ with a thin wall. As a result, the heat-transfer efficiency at the cooling liquid tubes $3b1'$ and $3c1'$ can be increased. However, as shown in FIG. 10, as the number of the tubes exceeds more than 50, the occupied area increases above the relative value when the number of tubes is 50. Consequently, it is preferable to use the number of the coolant outward path tubes $3b1'$ or the coolant return path tubes $3c1'$ within a range from 7 to 50.

Meanwhile, since it costs more to make the cooling paths by a multiplicity of thin tubes $3b1'$ and $3c1'$, a tradeoff arises with the performance. Under consideration of the cost of the cable 3', it is desirable to achieve the ultrasound probe by a necessary minimum number of thin tubes $3b1'$ and $3c1'$. Thus, it is desirable to make each of the cylindrical thin tubes $3b1'$ and $3c1'$ within a number range from 7 to 50, and each of the external diameter of the tubes $3b1$ and $3c1$ is within a range from $0.38 (=0.28+0.05\times2)$ mm to $1.35 (=0.75+0.3\times2)$ mm. It is also desirable to make each of the internal diameter of the tubes 3b1 and 3c1 is within a range from 0.28 mm to 0.75.

Other embodiments consistent with the present invention will be apparent to those skilled in the art from consideration of the specification and practice of the present invention disclosed herein. It is intended that the specification and examples be considered as exemplary only, with the true scope and spirit of the present invention being indicated by the following claims.

What is claimed is:

1. An ultrasound probe comprising:
   a handle unit including a plurality of transducers to transmit and receive ultrasound;
   a flexible cable directly connected to the handle unit;
   a connector unit directly connected to the cable for coupling the flexible cable to an ultrasound diagnosis apparatus; and
   a cooling liquid circulating system configured to circulate a liquid between the handle unit and the connector unit;
   wherein the cable includes a plurality of electric signal lines and a liquid circulation flow channel for the cooling liquid circulating system;
   wherein the liquid circulation flow channel is comprised of;
   a cooling liquid outward path configured to flow the cooling liquid from the connector unit to the handle unit, and
   a cooling liquid return path configured to flow the liquid from the handle unit to the connector unit,
   wherein at least either one of the cooling liquid outward path and the liquid return path is consisting of a plurality of thin flow tubes having a substantially smaller diameter than that of the cable and the plurality of the electric signal lines.

2. The ultrasound probe according to claim 1, wherein the liquid circulation flow channel is comprised of a first tube collective entity of the plurality of the thin tubes constructing the cooling liquid outward path and a second tube collective entity of the plurality of the thin tubes constructing the liquid return path,
   wherein the first tube collective entity and the second tube collective entity are provided apart with each other in the flexible cable.

3. The ultrasound probe according to claim 1, wherein the return path is comprised of a plurality of thin tubes, wherein the plurality of the thin tubes is provided in the flexible cable in a circular shape having a small tolerance space with each other near an envelope of the flexible cable.

4. The ultrasound probe according to claim 1, wherein the cooling liquid circulation system includes a pump configured to circulate the cooling liquid in the connector unit, and
   a first tube collective entity of the plurality of the thin tubes constructing the cooling liquid outward path and a second tube collective entity of the plurality of the thin tubes constructing the liquid return path connected to the pump.

5. The ultrasound probe according to claim 1, wherein each of the plurality of the thin tubes is formed in a cylindrical shape,
   wherein the plurality of the thin tubes is constructed by a number of the thin tubes within a range from seven (7) to fifty (50), and
   each of the plurality of the thin tubes has an external diameter within a range from 0.38 millimeter to 1.35 millimeters, and has an internal diameter within a range from 0.28 millimeter to 0.75 millimeter.

6. The ultrasound probe according to claim 1, wherein each of the plurality of thin the tubes is made of polyimide resin.

7. A cable for connecting an ultrasound probe comprising:
   electric cables each having an external cable diameter for transmitting electrical signals;
   a first cooling liquid path located at a first location within the cable for flowing a cooling liquid in a first direction along the cable; and
   a second cooling liquid path located at a second location within the cable for flowing the cooling liquid in a second direction that is opposite to the first direction along the cable, wherein at least one of said first cooling path and said second cooling path further consists of the electrical cables and a plurality of tubes ranging from seven (7) to fifty (50) in number and each of the tubes whose external diameter ranges from 0.38 millimeter to 1.35 millimeters and an internal diameter ranges from 0.28 millimeter to 0.75 millimeter.

8. The cable for connecting an ultrasound probe according to claim 7 wherein the first location and second location are apart from each other.

9. The cable for connecting an ultrasound probe according to claim 7 wherein said electric cables are located between the first location and the second location.

10. The cable for connecting an ultrasound probe according to claim 7 wherein either one of the first location and the second location is circular along an inner surface of the cable.

11. The cable for connecting an ultrasound probe according to claim 7 wherein said first cooling liquid path provides a certain space where said tubes move so as to avoid said tubes from being deformed when the cable is bent.

12. The cable for connecting an ultrasound probe according to claim 7 wherein said second cooling liquid path provides a certain space where said tubes move so as to avoid said tubes from being deformed when the cable is bent.

13. The cable for connecting an ultrasound probe according to claim 7 wherein said tube is made of flexible material.

* * * * *